US012692245B2

(12) United States Patent
Shioiri et al.

(10) Patent No.: US 12,692,245 B2
(45) Date of Patent: Jul. 28, 2026

(54) THIOPHENE COMPOUND, METHOD FOR SYNTHESIZING SAME, AND COMPOSITION CONTAINING SAID THIOPHENE COMPOUND

(71) Applicant: SHIKOKU CHEMICALS CORPORATION, Kagawa (JP)

(72) Inventors: Ryosuke Shioiri, Kagawa (JP); Takashi Kashiwabara, Kagawa (JP); Kazunori Aoki, Kagawa (JP); Takeshi Kumano, Kagawa (JP)

(73) Assignee: SHIKOKU CHEMICALS CORPORATION, Kagawa (JP)

( * ) Notice: Subject to any disclaimer, the term of this patent is extended or adjusted under 35 U.S.C. 154(b) by 322 days.

(21) Appl. No.: 18/698,246

(22) PCT Filed: Oct. 14, 2022

(86) PCT No.: PCT/JP2022/038356
§ 371 (c)(1),
(2) Date: Apr. 3, 2024

(87) PCT Pub. No.: WO2023/074408
PCT Pub. Date: May 4, 2023

(65) Prior Publication Data

US 2024/0400535 A1 Dec. 5, 2024

(30) Foreign Application Priority Data

Oct. 28, 2021 (JP) ................................. 2021-176990

(51) Int. Cl.
*C07D 333/38* (2006.01)
*C08F 12/30* (2006.01)

(52) U.S. Cl.
CPC ............ *C07D 333/38* (2013.01); *C08F 12/30* (2013.01)

(58) Field of Classification Search
CPC .............................. C07D 333/38; C08F 12/30
See application file for complete search history.

(56) References Cited

U.S. PATENT DOCUMENTS

2002/0010281 A1 1/2002 Musa et al.
2007/0060683 A1 3/2007 Musa et al.

FOREIGN PATENT DOCUMENTS

| | | | |
|---|---|---|---|
| CN | 101747461 | A | 6/2010 |
| JP | H01-118802 | A | 5/1989 |
| JP | 2008-094987 | A | 4/2008 |
| JP | 2008-241869 | A | 10/2008 |
| JP | 2009-057565 | A | 3/2009 |
| JP | 2010-248358 | A | 11/2010 |
| JP | 2016-056106 | A | 4/2016 |
| JP | 2021-100094 | A | 7/2021 |
| WO | WO 2009/017719 | A2 | 2/2009 |
| WO | WO 2011/055792 | A1 | 5/2011 |
| WO | WO 2020/028814 | A1 | 2/2020 |

OTHER PUBLICATIONS

CAS Registry No. 2183199-68-8 (which entered STN Mar. 2, 2018). (Year: 2018).*
Hiroyoshi Kamogawa et al., Vinyl Polymers Bearing Pyrrole Ring: I. Syntheses of Pyrroles Having 3-Substituent Bearing Vinyl Group, Bulletin of the Chemical Society of Japan, 1991, pp. 1066-1068, vol. 64, No. 3.
Jul. 25, 2025, European Search Report issued for related EP Application No. 22886737.0.

(Continued)

*Primary Examiner* — Kamal A Saeed
*Assistant Examiner* — Quincy McKoy
(74) *Attorney, Agent, or Firm* — Paratus Law Group, PLLC

(57) ABSTRACT

An object of the present invention is to provide a novel thiophene compound, a method for synthesizing the thiophene compound, and a composition containing the thiophene compound. The composition of the present invention has applications such as in coating materials, ink, adhesives, tackifiers, gas barrier films, color filters, optical films, optical lenses, and touch panels. The present invention relates to a thiophene compound represented by chemical formula (I) or chemical formula (II):

(I)

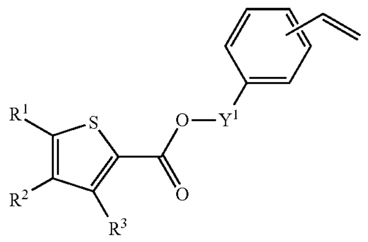

(II)

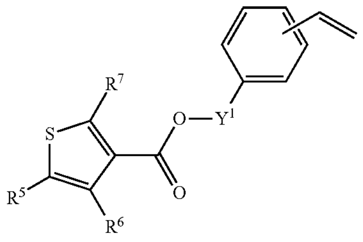

3 Claims, 2 Drawing Sheets

(56) References Cited

OTHER PUBLICATIONS

Malenfant et al., Well-Defined Triblock Hybrid Dendrimers Based on Lengthy Oligothiophene Cores and Poly(benzylether) Dendrons, Journal of the American Chemical Society, 1998, pp. 10990-10991, vol. 120, No. 42.
Deng et al., Discovery of 2-(4-Methylfuran-2(5H)-ylidene)malononitrile and Thieno[3,2-b]thiophene-2-carboxylic Acid Derivatives as G Protein-Coupled Receptor 35 (GPR35) Agonists, Journal of Medicinal Chemistry, 2011, pp. 7385-7396, vol. 54, No. 20.
McLeod et al., 4-Vinylphenyl Glycidyl Ether: Synthesis, RAFT Polymerization, and Postpolymerization Modifications with Alcohols, Macromolecules, 2016, pp. 1135-1142, vol. 49, No. 4.
Nov. 29, 2022, Translation of International Search Report issued for related PCT Application No. PCT/JP2022/038356.

* cited by examiner

THIOPHENE COMPOUND, METHOD FOR SYNTHESIZING SAME, AND COMPOSITION CONTAINING SAID THIOPHENE COMPOUND

CROSS REFERENCE TO PRIOR APPLICATION

This application is a National Stage Patent Application of PCT International Patent Application No. PCT/JP2022/038356 (filed on Oct. 14, 2022) under 35 U.S.C. § 371, which claims priority to Japanese Patent Application No. 2021-176990 (filed on Oct. 28, 2021), which are all hereby incorporated by reference in their entirety.

TECHNICAL FIELD

The present invention relates to a novel thiophene compound, a method for synthesizing the thiophene compound, and a composition containing the thiophene compound.

BACKGROUND ART

Thiophene compounds, which have a ring containing a sulfur element in their structure, have been considered for various applications due to the characteristic structure and have been studied, in particular, as lead compounds for pharmaceuticals, such as anticancer drugs (see, for example, PTL 1).

A variety of materials are used in resins for optical materials for use in various optical films and optical lenses. In general, such materials are polymerizable monomers, whose polymerization proceeds with radical species; materials with a high refractive index, such as those containing a polymerizable functional group (e.g., sulfur-containing compounds, fluorene compounds, and naphthalene compounds), are suitable for improving light extraction efficiency (e.g., PTL 2 to 5).

However, many of the materials with a high refractive index reported so far have a high melting point or high viscosity, making the molding process long and work efficiency low. Therefore, from the viewpoint of improving work efficiency, there is demand for materials having a polymerizable functional group with a high refractive index while having a lower melting point and lower viscosity.

CITATION LIST

Patent Literature

PTL 1: WO2020/028814A
PTL 2: JP2016-56106A
PTL 3: JP2008-94987A
PTL 4: JP2010-248358A
PTL 5: JPH01-118802A

SUMMARY OF INVENTION

Technical Problem

An object of the present invention is to provide a novel thiophene compound, a method for synthesizing the thiophene compound, and a composition containing the thiophene compound. The composition of the present invention has applications such as in coating materials, ink, adhesives, tackifiers, gas barrier films, color filters, optical films, optical lenses, and touch panels.

Solution to Problem

The present inventors conducted extensive research to achieve the object and recognized a thiophene compound obtained by reacting a specific thiophene compound with a specific styrene compound as being able to achieve the intended purpose. The inventors then completed the present invention.

Specifically, the first invention is a thiophene compound represented by chemical formula (I) or chemical formula (II):

(I)

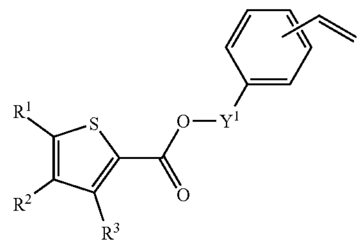

wherein $R^1$, $R^2$, and $R^3$ are identical or different and represent a hydrogen atom, —$OR^4$, —$SR^4$, —C(═O)—$R^4$, a phenyl group, a 2-thienyl group, or a 3-thienyl group, $R^2$ may be linked with $R^1$ or $R^3$ to form a ring containing a sulfur atom, together with two thiophene ring-forming carbon atoms to which $R^2$ and either $R^1$ or $R^3$ are bonded, $R^4$s are identical or different and represent a $C_{1-5}$ alkyl group, and $Y^1$ represents a single bond or a $C_{1-10}$, alkylene group; and (II)

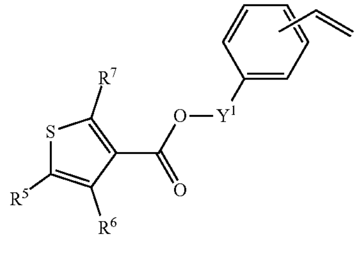

wherein $R^5$, $R^6$, and $R^7$ are identical or different and represent a hydrogen atom, —$OR^4$, —$SR^4$, —C(═O)—$R^4$, a phenyl group, a 2-thienyl group, or a 3-thienyl group, $R^5$ may be linked with $R^1$ to form a ring containing a sulfur atom, together with two thiophene ring-forming carbon atoms to which $R^5$ and $R^6$ are bonded, $R^4$s are identical or different and represent a $C_{1-5}$ alkyl group, and $Y^1$ represents a single bond or a $C_{1-10}$ alkylene group.

The second invention is a method for synthesizing the thiophene compound of the first invention, the method comprising reacting a thiophene compound represented by chemical formula (III) or chemical formula (IV) with a styrene compound represented by chemical formula (V):

(III)

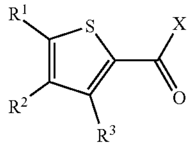

wherein $R^1$, $R^2$, and $R^3$ are as defined above, X represents a hydroxy group, a fluorine atom, a chlorine atom, a bromine atom, or an iodine atom;

(IV)

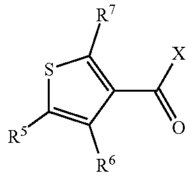

wherein $R^5$, $R^6$, and $R^7$ are as defined above, X represents a hydroxy group, a fluorine atom, a chlorine atom, a bromine atom, or an iodine atom; and (V)

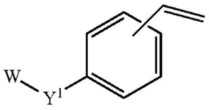

wherein $Y^1$ is as defined above, and W represents a hydroxy group, a fluorine atom, a chlorine atom, a bromine atom, or an iodine atom.

The third invention is a composition comprising the thiophene compound of the first invention.

Advantageous Effects of Invention

The thiophene compound of the present invention is expected to be useful as a material in optical applications because of its high refractive index and low viscosity.

The composition containing the thiophene compound of the present invention is also expected to improve workability during molding due to its lower viscosity than that of conventional compositions. Additionally, the composition is also expected to provide a cured product with a high refractive index.

DESCRIPTION OF EMBODIMENTS

Figure 1:
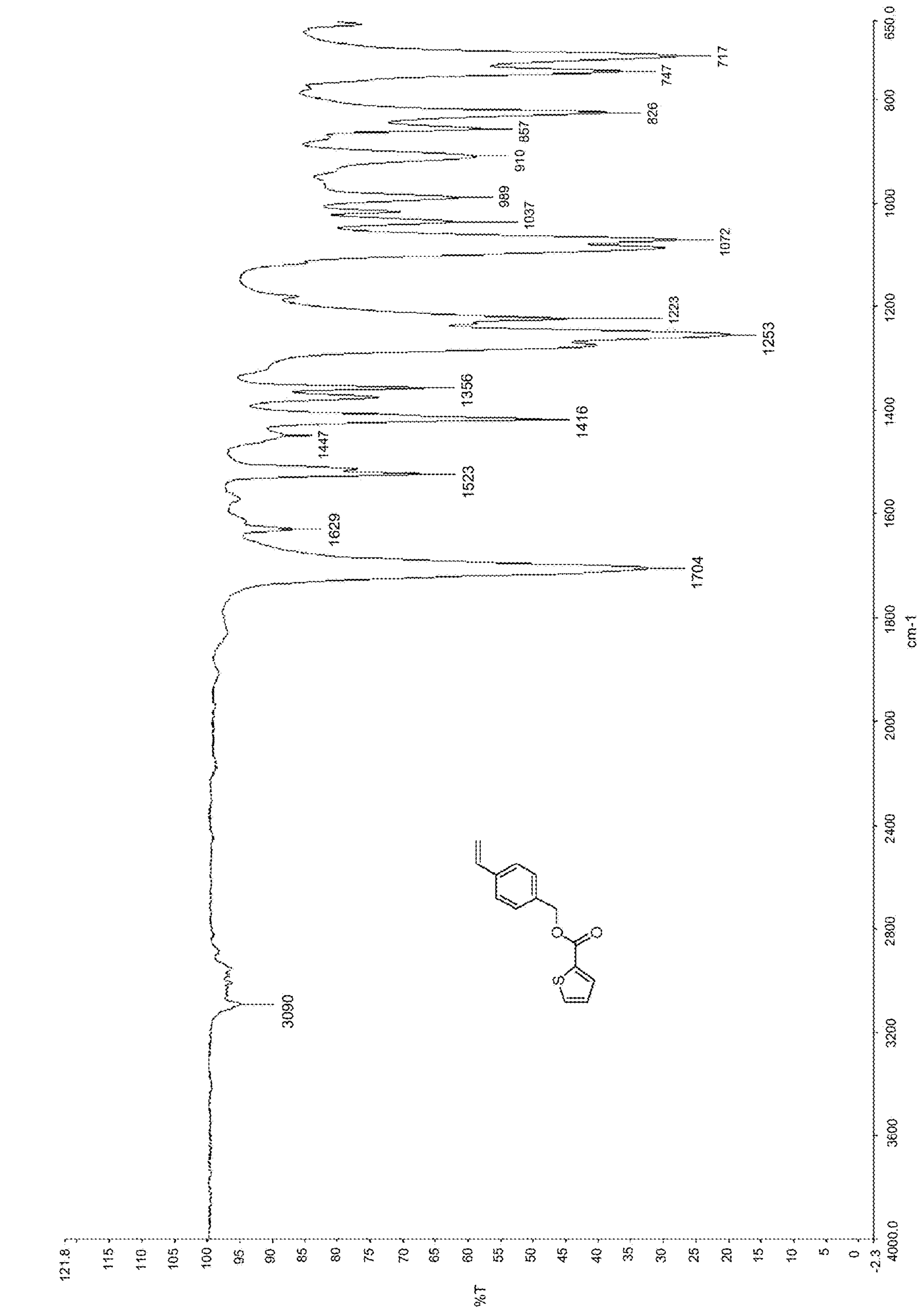
FIG. 1: An IR spectrum chart of the pale yellow liquid obtained in Example 1

The present invention is described in detail below.

The present invention relates to a thiophene compound represented by chemical formula (I) or chemical formula (II) ("the thiophene compound of the present invention" below).

Examples of the thiophene compound represented by chemical formula (I) include thiophene compounds represented by chemical formula (I-1) to chemical formula (I-30).

Examples of the thiophene compound represented by chemical formula (II) include thiophene compounds represented by chemical formula (II-1) to chemical formula (II-27).

(I-1)

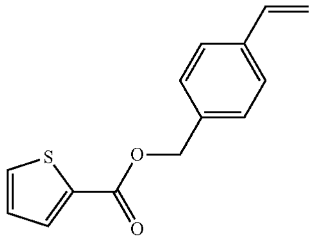

(I-2)

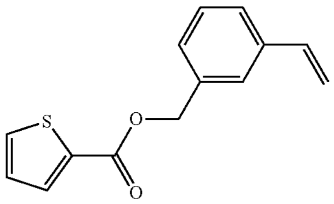

(I-3)

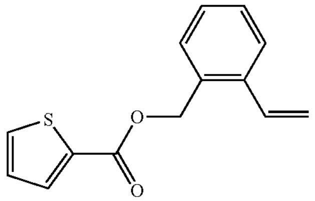

(I-4)

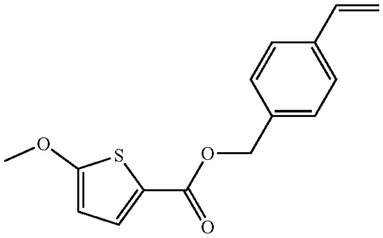

(I-5)

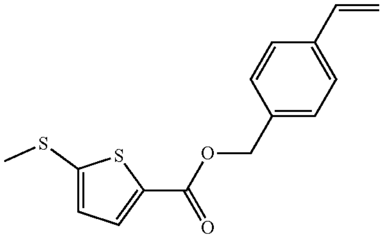

(I-6)

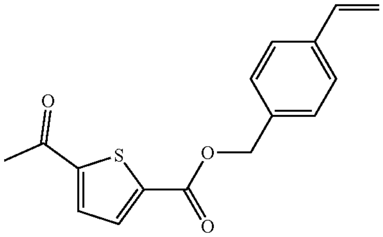

-continued
(I-7)
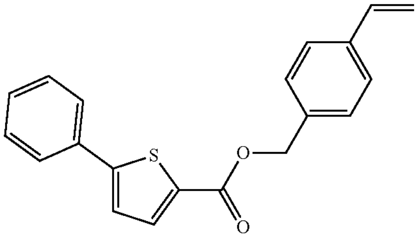
(I-8)
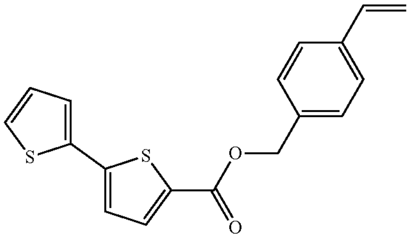
(I-9)
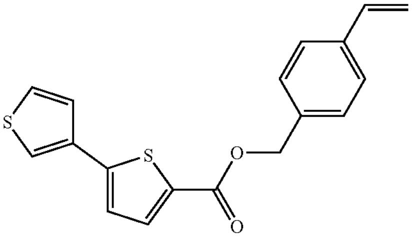
(I-10)
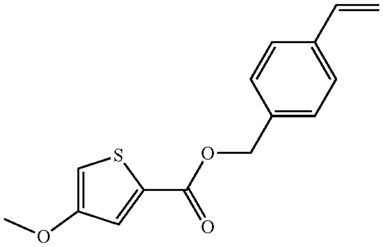
(I-11)
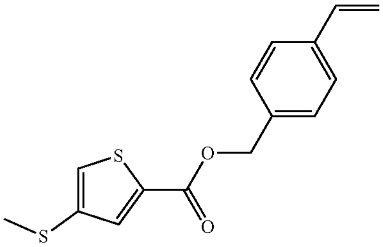
(I-12)
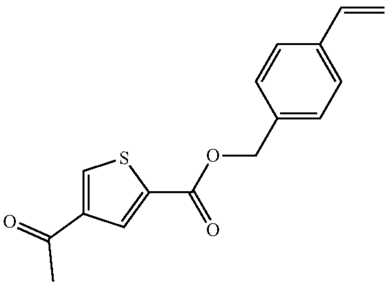
-continued
(I-13)
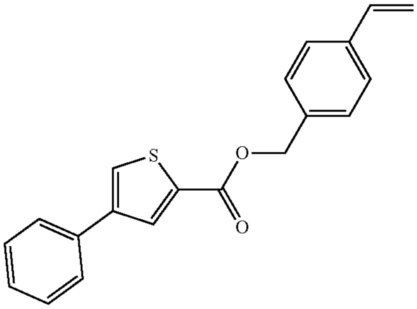
(I-14)
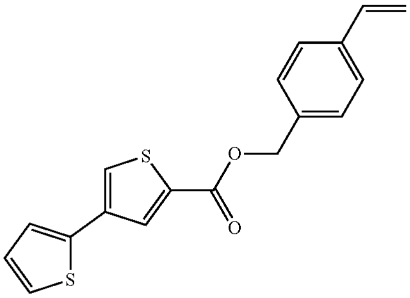
(I-15)
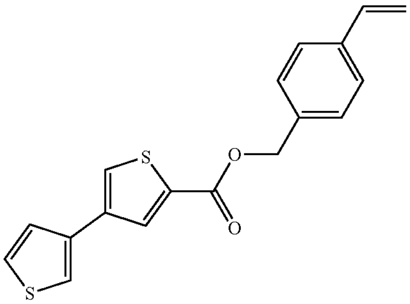
(I-16)
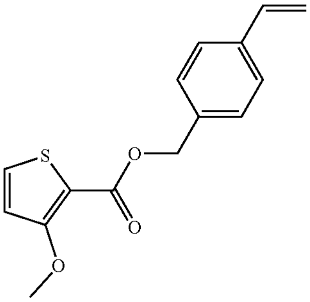
(I-17)
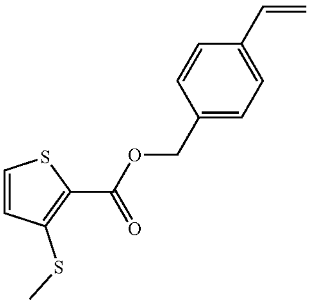

-continued
(I-18)
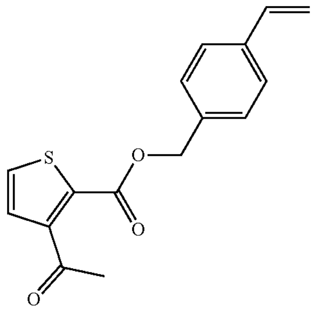
(I-19)
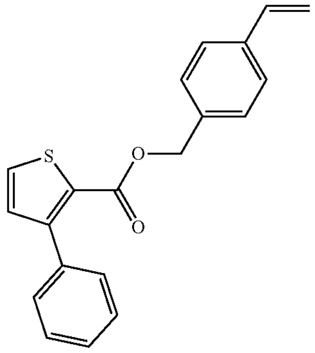
(I-20)
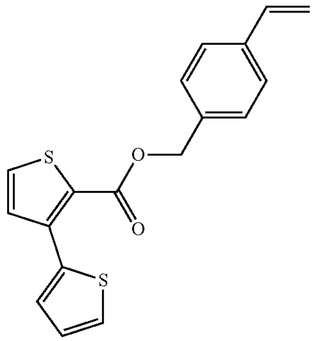
(I-21)
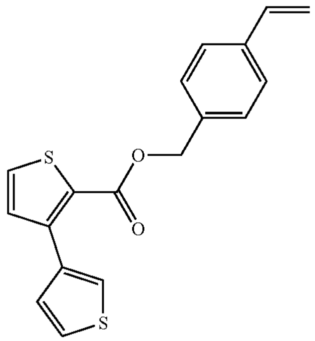
(I-22)
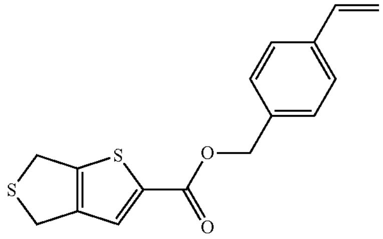
-continued
(I-23)
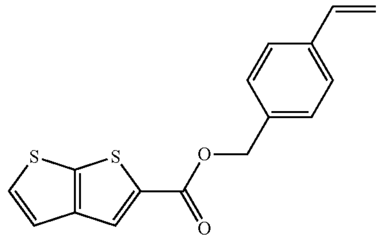
(I-24)
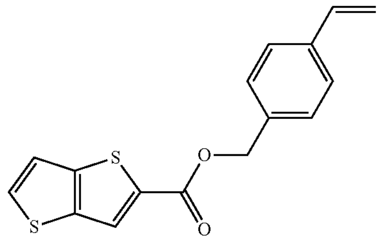
(I-25)
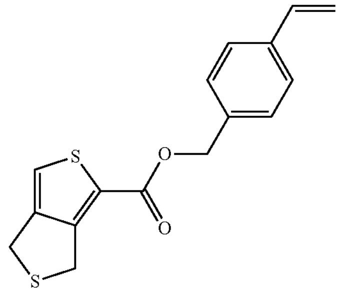
(I-26)
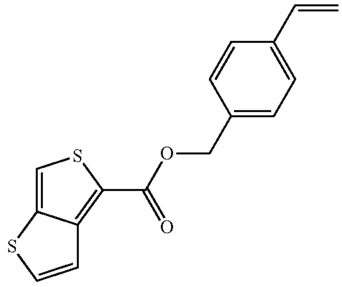
(I-27)
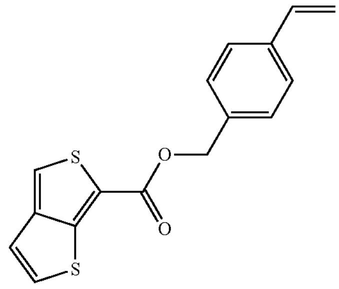
(I-28)
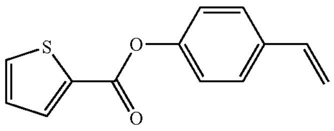

-continued
(I-29)
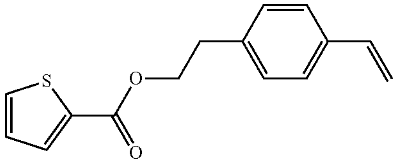
(I-30)
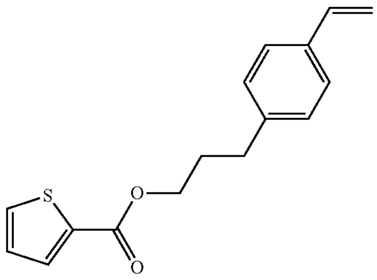
(II-1)
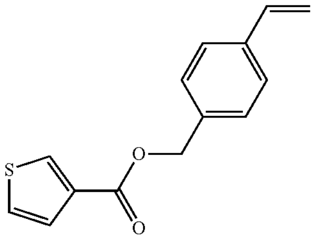
(II-2)
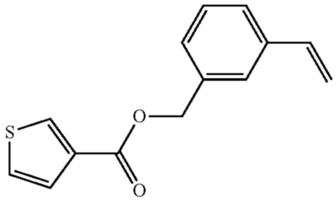
(II-3)
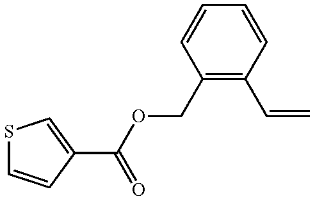
(II-4)
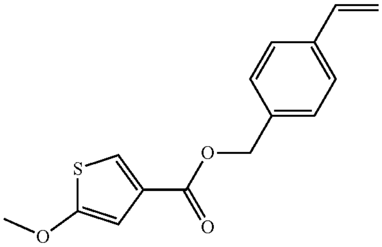
(II-5)
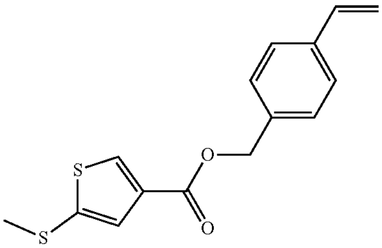
-continued
(II-6)
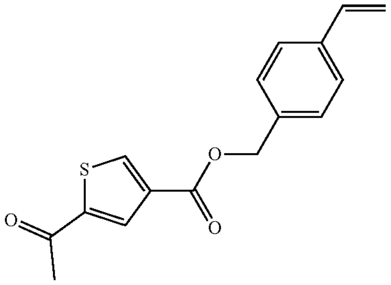
(II-7)
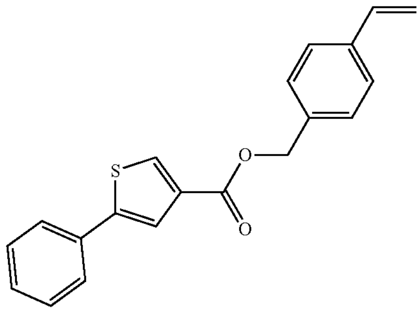
(II-8)
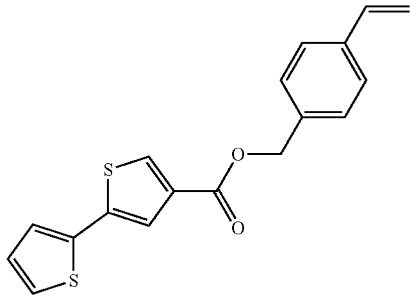
(II-9)
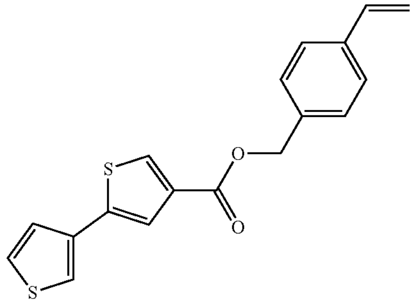
(II-10)
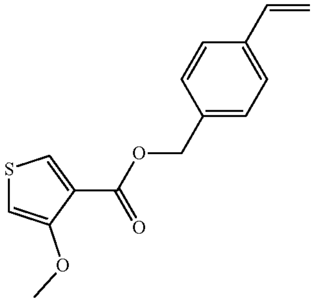

-continued
(II-11)
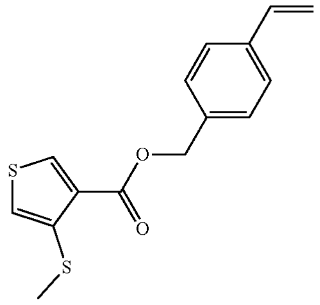
(II-12)
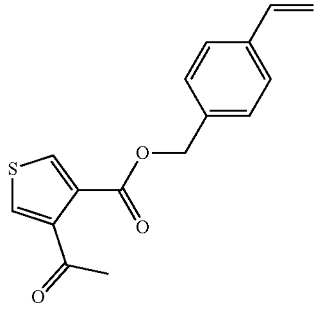
(II-13)
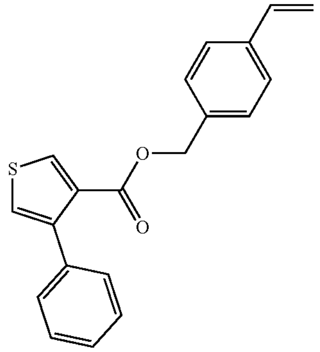
(II-14)
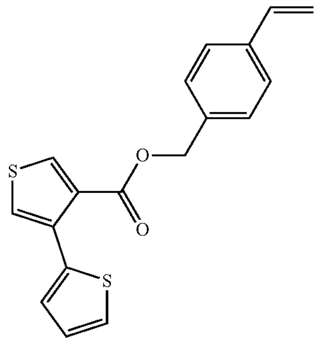
-continued
(II-15)
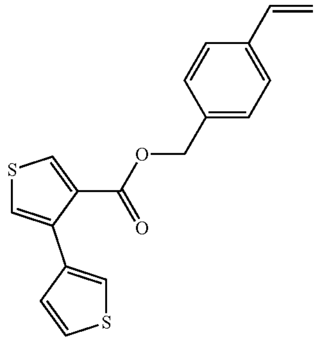
(II-16)
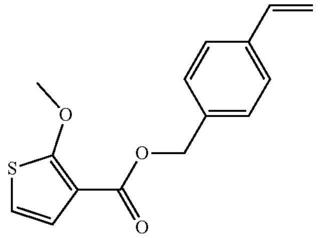
(II-17)
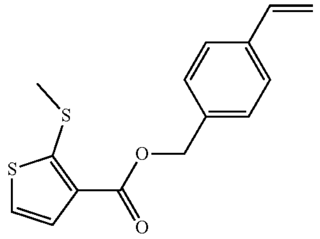
(II-18)
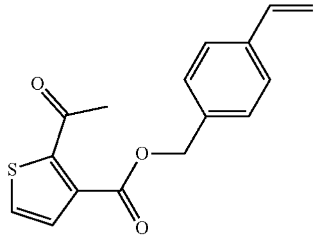
(II-19)
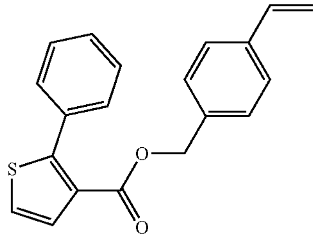
(II-20)
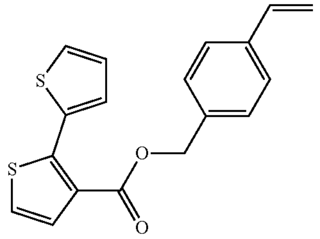

-continued (II-21)

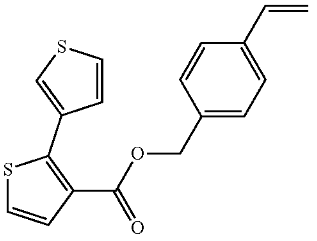

(II-22)

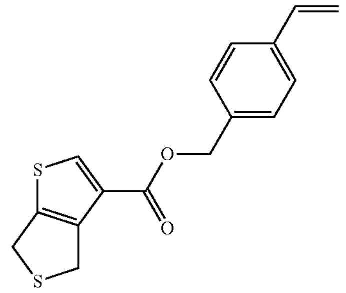

(II-23)

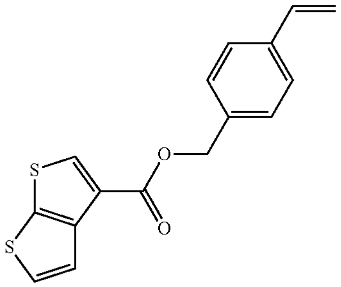

(II-24)

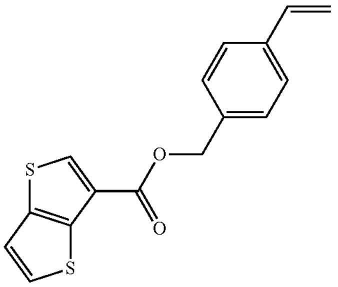

(II-25)

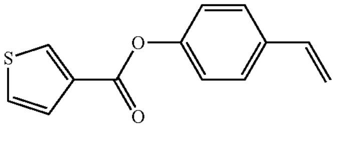

(II-26)

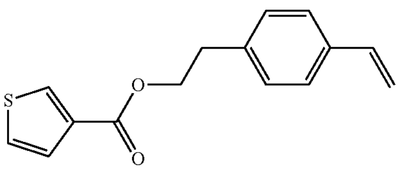

-continued (II-27)

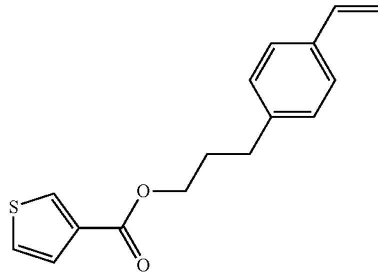

As defined above, $R^2$ may be linked with $R^1$ or $R^3$ to form a ring containing a sulfur atom, together with two thiophene ring-forming carbon atoms to which $R^2$ and either $R^1$ or $R^3$ are bonded. If $R^2$ is linked with $R^1$ to form a ring containing a sulfur atom, the divalent group formed by $R^2$ linked with $R^2$ includes those represented by the following formulas (a) to (c). If $R^2$ is linked with $R^3$ to form a ring containing a sulfur atom, the divalent group formed by $R^2$ linked with $R^3$ includes those represented by the following formulas (a) to (c).

(a)

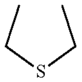

(b)

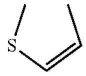

(c)

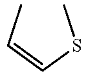

The $C_{1-5}$ alkyl group represented by $R^4$ includes linear or branched $C_{1-5}$ alkyl groups, specifically, such as a methyl group, an ethyl group, an n-propyl group, an isopropyl group, an n-butyl group, a t-butyl group, and an n-pentyl group.

As defined above, $R^5$ may be linked with $R^6$ to form a ring containing a sulfur atom, together with two thiophene ring-forming carbon atoms to which $R^5$ and $R^6$ are bonded. If $R^5$ is linked with $R^6$ to form a ring containing a sulfur atom, the divalent group formed by $R^5$ linked with $R^6$ includes those represented by formulas (a) to (c) above.

The $C_{1-10}$, alkylene group represented by $Y^1$ includes linear or branched $C_{1-10}$ alkylene groups (preferably $C_{1-6}$ alkylene groups, more preferably $C_{1-4}$ alkylene groups, and particularly preferably $C_{1-3}$ alkylene groups), specifically, such as a methylene group, a methyl methylene group, a dimethylene group, a trimethylene group, an ethyl methylene group, a dimethyl methylene group, a tetramethylene group, a pentamethylene group, a hexamethylene group, a heptamethylene group, an octamethylene group, a nonamethylene group, and a decamethylene group.

In the thiophene compound represented by chemical formula (I), preferable substituents are as described below.

$R^1$, $R^2$, and $R^3$ are identical or different and preferably represent a hydrogen atom, —$OR^4$, —$SR^4$, —C(═O)—$R^4$, a phenyl group, a 2-thienyl group, or a 3-thienyl group.

Alternatively, $R^1$, $R^2$, and $R^3$ are all a hydrogen atom, or two of $R^1$, $R^2$, and $R^3$ are a hydrogen atom with the remaining one group being preferably —$OR^4$, —$SR^4$, —C(═O)—$R^4$, a phenyl group, a 2-thienyl group, or a 3-thienyl group.

Alternatively, among $R^1$, $R^2$, and $R^3$, $R^2$ is linked with $R^1$ or $R^3$ to form a ring containing a sulfur atom, together with two thiophene ring-forming carbon atoms to which $R^2$ and either $R^1$ or $R^3$ are bonded, and the divalent group formed by $R^2$ linked with $R^1$ or $R^3$ is represented by formulas (a) to (c), with the remaining $R^3$ or $R^1$ being preferably a hydrogen atom, —$OR^4$, —$SR^4$, —C(═O)—$R^4$, a phenyl group, a 2-thienyl group, or a 3-thienyl group, and more preferably a hydrogen atom.

$R^4$ is preferably a $C_{1-3}$ alkyl group, and more preferably a methyl group.

$Y^1$ is preferably a single bond or a $C_{1-4}$ (more preferably $C_{1-3}$) alkylene group.

The thiophene compound represented by chemical formula (I) is more preferably a thiophene compound represented by any of chemical formulas (I-1) to (I-3), (I-5), (I-8), (I-9), and (I-22) to (I-24).

In the thiophene compound represented by chemical formula (II), preferable substituents are as described below.

$R^5$, $R^6$, and $R^7$ are identical or different and preferably represent a hydrogen atom, —$OR^4$, —$SR^4$, —C(═O)—$R^4$, a phenyl group, a 2-thienyl group, or a 3-thienyl group.

Alternatively, $R^5$, $R^6$, and $R^7$ are all a hydrogen atom, or two of $R^5$, $R^6$, and $R^7$ are a hydrogen atom with the remaining one group being preferably —$OR^4$, —$SR^4$, —C(═O)—$R^4$, a phenyl group, a 2-thienyl group, or a 3-thienyl group.

Alternatively, among $R^5$, $R^6$, and $R^7$, $R^5$ is linked with $R^6$ to form a ring containing a sulfur atom, together with two thiophene ring-forming carbon atoms to which $R^5$ and $R^6$ are bonded, and the divalent group formed by $R^5$ linked with $R^6$ is represented by formulas (a) to (c), with the remaining $R^7$ being preferably a hydrogen atom, —$OR^4$, —$SR^4$, —C(═O)—$R^4$, a phenyl group, a 2-thienyl group, or a 3-thienyl group, and more preferably a hydrogen atom.

$R^1$ is preferably a $C_{1-3}$ alkyl group, and more preferably a methyl group.

$Y^1$ is preferably a single bond or a $C_{1-4}$ (more preferably $C_{1-3}$) alkylene group.

The thiophene compound represented by chemical formula (II) is more preferably a thiophene compound represented by any of chemical formulas (II-1) to (II-3), (II-5), (II-8), (II-9), and (II-22) to (II-24).

The thiophene compound of the present invention can be synthesized by reacting a thiophene compound represented by chemical formula (III) or chemical formula (IV) with a styrene compound represented by chemical formula (V).

The thiophene compound represented by chemical formula (III) is a precursor of the thiophene compound represented by chemical formula (I), and the thiophene compound represented by chemical formula (IV) is a precursor of the thiophene compound represented by chemical formula (II).

The thiophene compound represented by chemical formula (III) encompasses thiophene compounds represented by chemical formula (III-1), which have a halogenated acyl group, (a thiophene compound wherein X represents a fluorine atom, a chlorine atom, a bromine atom, or an iodine atom) and thiophene compounds represented by chemical formula (III-2), which have a carboxy group, (a thiophene compound wherein X represents a hydroxy group).

The thiophene compound represented by chemical formula (IV) encompasses thiophene compounds represented by chemical formula (IV-1), which have a halogenated acyl group, (a thiophene compound wherein X represents a fluorine atom, a chlorine atom, a bromine atom, or an iodine atom) and thiophene compounds represented by chemical formula (IV-2), which have a carboxy group, (a thiophene compound wherein X represents a hydroxy group).

(III-1)

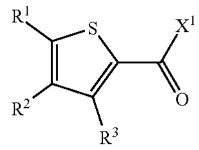

(III-2)

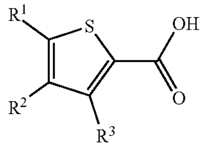

(IV-1)

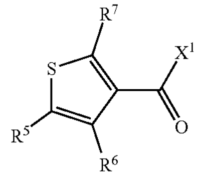

(IV-2)

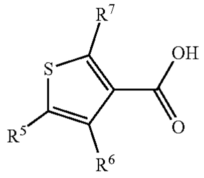

(wherein $R^1$, $R^2$, $R^3$, $R^5$, $R^6$, and $R^7$ are as defined above, and $X^1$ represents a fluorine atom, a chlorine atom, a bromine atom, or an iodine atom.)

Examples of the thiophene compound represented by chemical formula (III-1) include thiophene compounds represented by chemical formulas (III-1-1) to (III-1-18).

Examples of the thiophene compound represented by chemical formula (III-2) include thiophene compounds represented by chemical formulas (III-2-1) to (III-2-25).

Examples of the thiophene compound represented by chemical formula (III-1) include thiophene compounds represented by chemical formulas (IV-1-1) to (IV-1-9).

Examples of the thiophene compound represented by chemical formula (IV-2) include thiophene compounds represented chemical formulas (IV-2-1) to (IV-2-22).

(III-1-1)

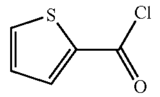

(III-1-2)

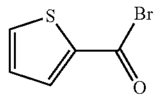

(III-1-3)

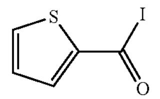

-continued
(III-1-4)
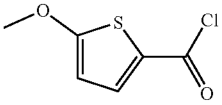
(III-1-5)
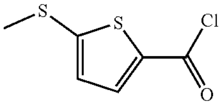
(III-1-6)
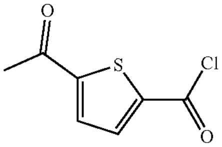
(III-1-7)
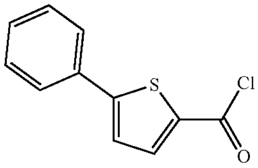
(III-1-8)
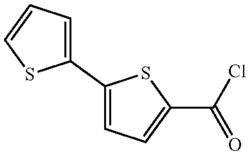
(III-1-9)
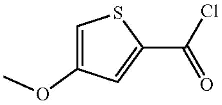
(III-1-10)
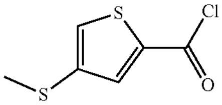
(III-1-11)
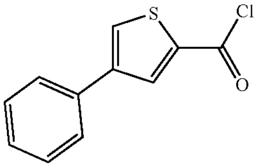
(III-1-12)
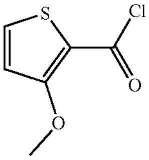
(III-1-13)
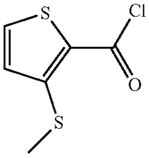
-continued
(III-1-14)
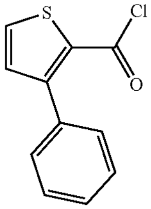
(III-1-15)
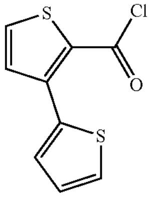
(III-1-16)
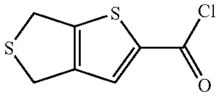
(III-1-17)
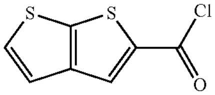
(III-1-18)
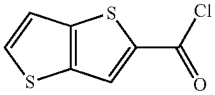
(III-2-1)
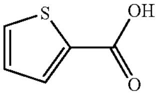
(III-2-2)
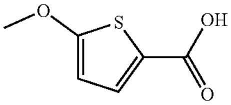
(III-2-3)
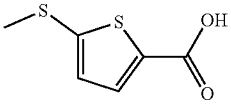
(III-2-4)
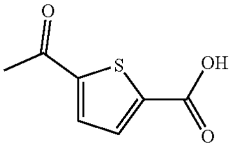
(III-2-5)
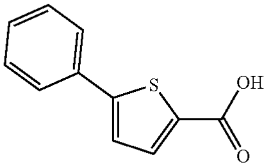
(III-2-6)
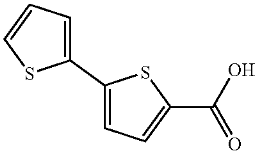

-continued
(III-2-7)
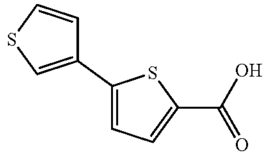
(III-2-8)
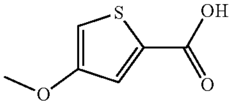
(III-2-9)
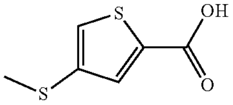
(III-2-10)
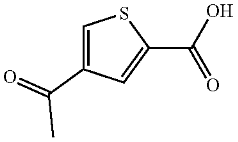
(III-2-11)
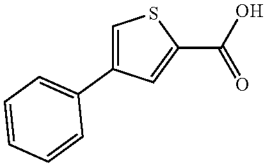
(III-2-12)
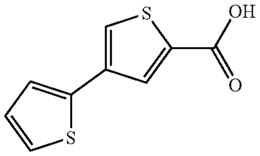
(III-2-13)
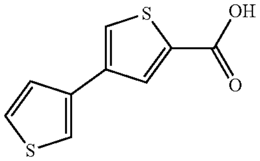
(III-2-14)
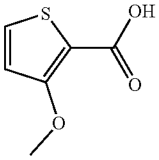
(III-2-15)
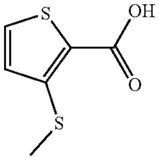
(III-2-16)
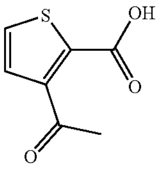
-continued
(III-2-17)
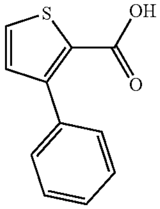
(III-2-18)
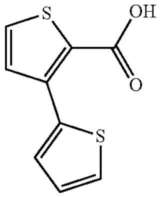
(III-2-19)
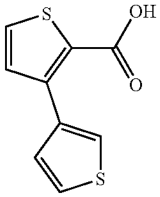
(III-2-20)
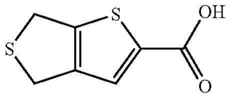
(III-2-21)
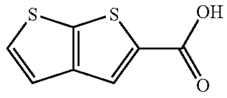
(III-2-22)
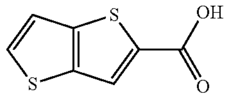
(III-2-23)
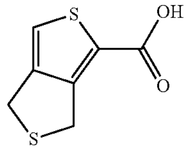
(III-2-24)
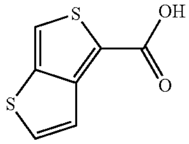
(III-2-25)
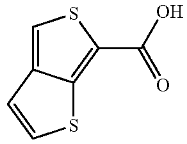
(IV-1-1)
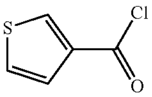

-continued
(IV-1-2)
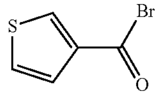
(IV-1-3)
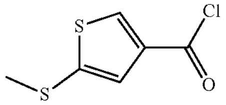
(IV-1-4)
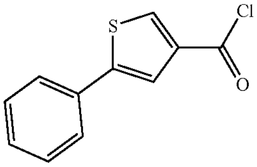
(IV-1-5)
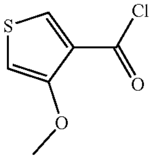
(IV-1-6)
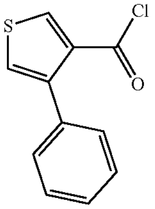
(IV-1-7)
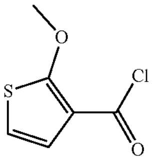
(IV-1-8)
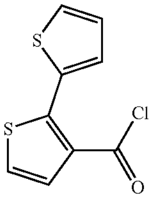
(IV-1-9)
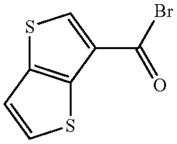
(IV-2-1)
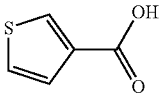
(IV-2-2)
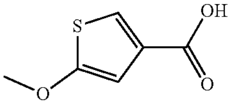
-continued
(IV-2-3)
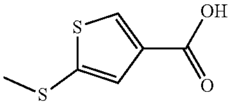
(IV-2-4)
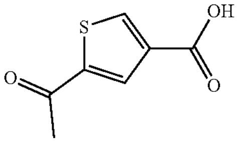
(IV-2-5)
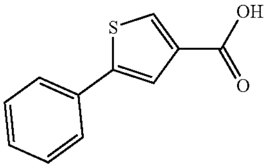
(IV-2-6)
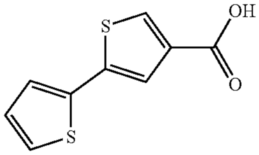
(IV-2-7)
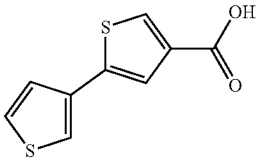
(IV-2-8)
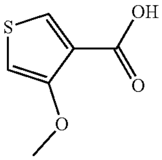
(IV-2-9)
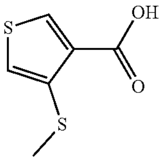
(IV-2-10)
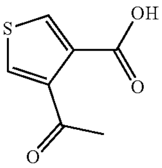
(IV-2-11)
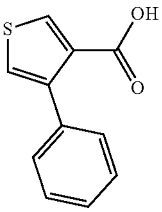

-continued (IV-2-12)

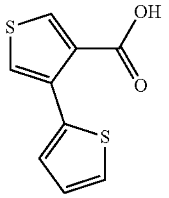

(IV-2-13)

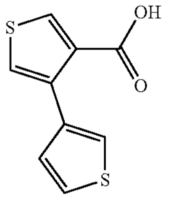

(IV-2-14)

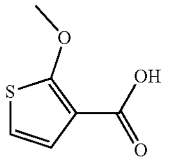

(IV-2-15)

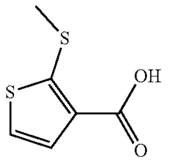

(IV-2-16)

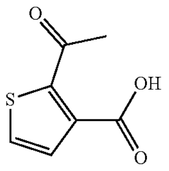

(IV-2-17)

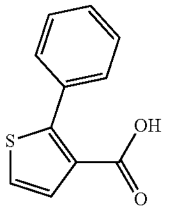

(IV-2-18)

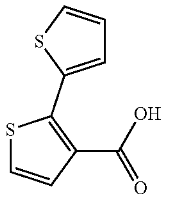

(IV-2-19)

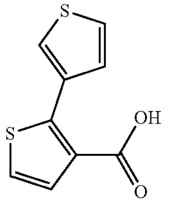

-continued (IV-2-20)

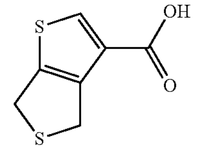

(IV-2-21)

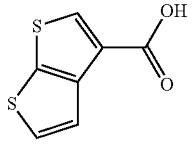

(IV-2-22)

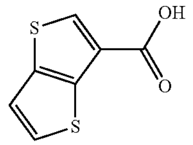

These thiophene compounds for use may be commercially available reagents purchased, or synthesized, for example, according to the method described later or the method described in the Journal of the American Chemical Society, 120(42), 10990-10991(1998), the Journal of Medicinal Chemistry, 54 (20), 7385-7396(2011), or JP22021-100094A.

The styrene compound represented by chemical formula (V) encompasses styrene compounds represented by chemical formula (V-1), which have a hydroxy group, (a styrene compound wherein W represents a hydroxy group) and styrene compounds represented by chemical formula (V-2), which have a halogen atom, (a styrene compound wherein W represents a fluorine atom, a chlorine atom, a bromine atom, or an iodine atom).

(V-1)

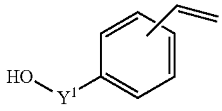

(V-2)

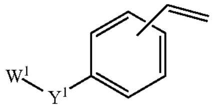

(wherein $Y^1$ is as defined above, and W=represents a fluorine atom, a chlorine atom, a bromine atom, or an iodine atom.)

Examples of the styrene compound represented by chemical formula (V-1) include styrene compounds represented by chemical formulas (V-1-1) to (V-1-6).

Examples of the styrene compound represented by chemical formula (V-2) include styrene compounds represented by (V-1-1)

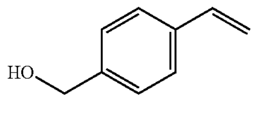

-continued (V-1-2)

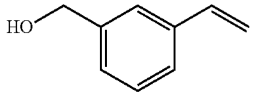

(V-1-3)

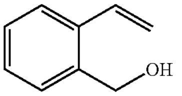

(V-1-4)

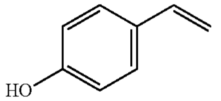

(V-1-5)

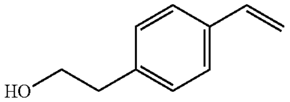

(V-1-6)

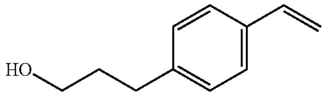

(V-2-1)

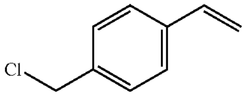

(V-2-2)

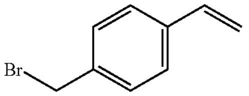

(V-2-3)

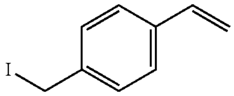

(V-2-4)

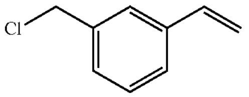

(V-2-5)

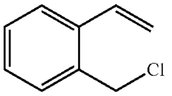

(V-2-6)

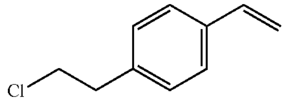

(V-2-7)

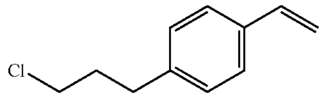

These styrene compounds for use may be commercially available reagents purchased, or synthesized, for example, according to the method described in WO2011/55792A, Macromolecules, 49(4), 1135-1142(2016), CN101747461A, or JP2009-57565A.

Examples of synthesis methods for the thiophene compound of the present invention include synthesis methods (1) to (4).

Synthesis Method (1)

A thiophene compound represented by chemical formula (III-1) or chemical formula (IV-1) is reacted with a styrene compound represented by chemical formula (V-1) to synthesize the thiophene compound of the present invention (see reaction schemes (A) and (B)).

Reaction Scheme (A)

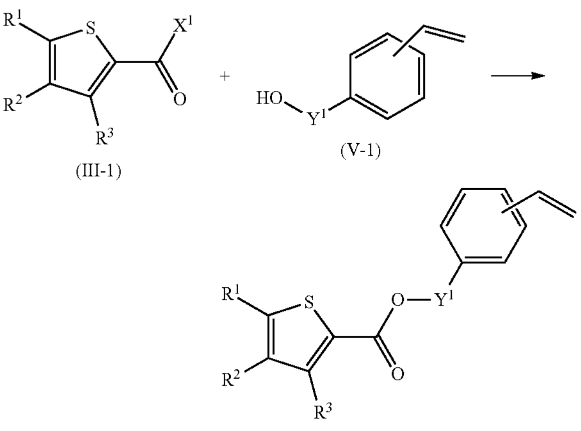

(III-1) (V-1) (I)

(wherein $R^1$, $R^2$, $R^3$, $Y^1$, and $X^1$ are as defined above.)

Reaction Scheme (B)

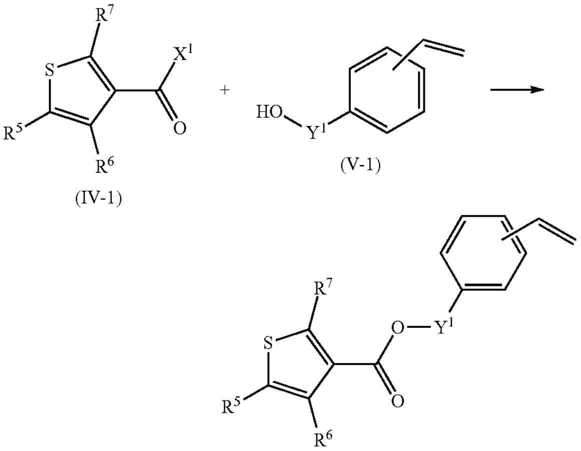

(IV-1) (V-1) (II)

(wherein $R^5$, $R^6$, $R^7$, $Y^1$, and $X^1$ are as defined above.)

In this reaction, the amount of the styrene compound represented by chemical formula (V-1) (the amount added) is preferably an appropriate proportion within the range of 0.8-fold to 1.2-fold mol relative to the amount of the thiophene compound represented by chemical formula (III-1) or chemical formula (IV-1) (the amount added).

In performing this reaction, it is preferable to use a base (i) in order to remove an acid (by-product) formed over the course of reaction. A reaction solvent (ii) may also be used as necessary.

Examples of the base (i) include trimethylamine, triethylamine, tributylamine, N,N-diisopropylethylamine, N-methylmorpholine, 1,5-diazabicyclo[4.3.0]non-5-ene (DBN), 1,4-diazabicyclo[2.2.2]octane (DABCO), 1,8-diazabicyclo[5.4.0]-7-undecene (DBU), pyridine, 4-(N, N-dimethylamino)pyridine, picoline, N,N-dimethylaniline, N,N- diethylaniline, imidazole, lithium hydride, sodium hydride, potassium hydride, lithium hydroxide, sodium hydroxide, potassium hydroxide, cesium hydroxide, lithium carbonate, sodium carbonate, potassium carbonate, cesium carbonate, lithium hydrogen carbonate, sodium hydrogen carbonate, potassium hydrogen carbonate, cesium hydrogen carbonate, trilithium phosphate, trisodium phosphate, tripotassium phosphate, tricesium phosphate, dilithium hydrogen phosphate, disodium hydrogen phosphate, dipotassium hydrogen phosphate, dicesium hydrogen phosphate, lithium dihydrogen phosphate, sodium dihydrogen phosphate, potassium dihydrogen phosphate, cesium dihydrogen phosphate, lithium acetate, sodium acetate, potassium acetate, cesium acetate, lithium alkoxide (e.g., lithium methoxide), sodium alkoxide (e.g., sodium methoxide and sodium ethoxide), and potassium alkoxide (e.g., potassium t-butoxide). These may be used singly, or in a combination of two or more.

The amount of the base (i) (the amount added) is preferably an appropriate proportion within the range of 0.8-fold to 2-fold mol relative to the amount of the thiophene compound represented by chemical formula (III-1) or chemical formula (IV-1) (the amount added).

The reaction solvent (ii) is not particularly limited as long as the reaction solvent (ii) does not interfere with the reaction. Examples of the reaction solvent (ii) include solvents such as tetrahydrofuran, dioxane, ethyl acetate, acetonitrile, benzene, toluene, xylene, dichloromethane, chloroform, carbon tetrachloride, dimethylformamide, dimethylacetamide, dimethylsulfoxide, hexamethylphosphoric triamide, and water. These can be combined as necessary and used in an appropriate amount.

In this reaction, the reaction temperature is preferably set within the range of 0 to 100° C. The reaction time is set as appropriate according to the predetermined reaction temperature and is preferably set within the range of 1 to 48 hours.

After completion of the reaction, the thiophene compound of the present invention (desired product) can be taken out from the obtained reaction solution (reaction mixture) according to a means such as concentration of the reaction solution by distillation of the reaction solvent or solvent extraction.

Additionally, the thiophene compound of the present invention can be purified according to a means such as washing with water etc., activated carbon treatment, silica gel chromatography, or recrystallization as necessary.

Synthesis Method (2)

A thiophene compound represented by chemical formula (III-2) or chemical formula (IV-2) is reacted with a halogenating agent (first step), and then the reaction product is reacted with a styrene compound represented by chemical formula (V-1) (second step) to synthesize the thiophene compound of the present invention (see reaction schemes (C) and (D)).

Reaction Scheme (C)

(First Step)

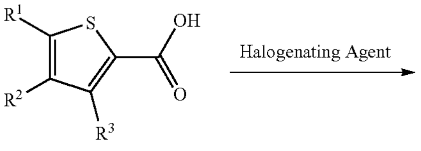

(III-2)

-continued

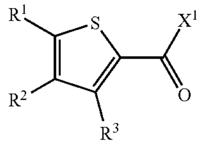

(III-1)

(Second Step)

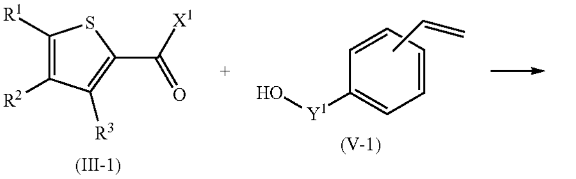

(III-1) (V-1)

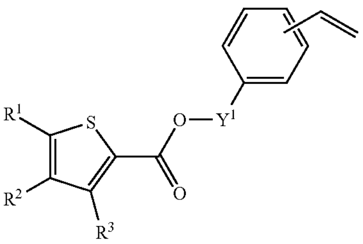

(I)

(wherein $R^1$, $R^2$, $R^3$, $Y^1$, and $X^1$ are as defined above.)

Reaction Scheme (D)

(First Step)

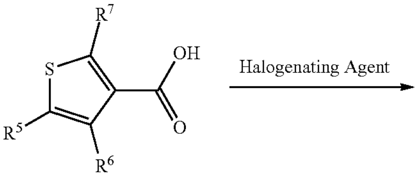

(IV-2)

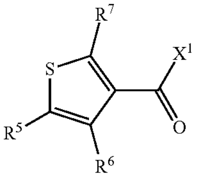

(IV-1)

(Second Step)

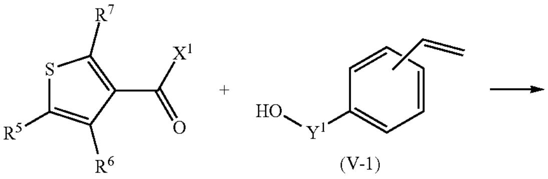

(IV-1) (V-1)

-continued

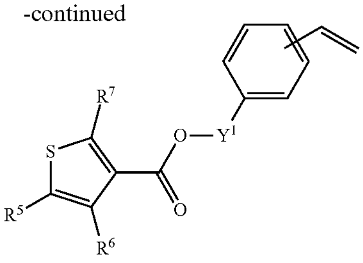

(II)

(wherein $R^5$, $R^6$, $R^7$, $Y^1$, and $X^1$ are as defined above.)

The halogenating agent can be any agent that can convert carboxylic acid to a carboxylic acid halide, and examples include fluorinating agents, chlorinating agents, and brominating agents. Specific examples include oxalyl chloride, thionyl chloride, and phosphoryl chloride. A catalytic amount of dimethylformamide or the like may be added to improve the reactivity of the halogenating agent.

In the reaction of the first step, the amount of the halogenating agent (the amount added) is preferably an appropriate proportion within the range of 1-fold to 10-fold mol relative to the amount of the thiophene compound represented by chemical formula (III-2) or chemical formula (IV-2) (the amount added).

In the reaction of the first step, a reaction solvent (iii) may be used as necessary. The reaction solvent (iii) is not particularly limited as long as the reaction solvent (iii) does not interfere with the reaction. Examples include solvents such as benzene, toluene, xylene, dichloromethane, chloroform, carbon tetrachloride, dimethylformamide, dimethylacetamide, and dimethylsulfoxide. These can be combined as necessary and used in an appropriate amount.

In the reaction of the first step, the reaction temperature is preferably set within the range of 0 to 120° C. The reaction time is set as appropriate according to the predetermined reaction temperature and is preferably set within the range of 1 to 48 hours.

After completion of the reaction in the first step, a thiophene compound having a halogenated acyl group (desired product) can be taken out from the obtained reaction solution (reaction mixture) according to a means such as concentration of the reaction solution by distillation of the reaction solvent or solvent extraction.

Additionally, the thiophene compound having a halogenated acyl group can be purified according to a means such as washing with water etc., activated carbon treatment, silica gel chromatography, or recrystallization as necessary.

After undergoing the concentration, extraction, purification, or the like, the thiophene compound having a halogenated acyl group may be subjected to the second step. Alternatively, after completion of the reaction in the first step, the obtained reaction solution, as is, may be subjected to the second step.

The reaction of the second step can be performed in the same manner as in Synthesis Method (1) described above.

In that manner, the thiophene compound of the present invention (desired product) can be obtained.

Synthesis Method (3)

A thiophene compound represented by chemical formula (III-2) or chemical formula (IV-2) is reacted with a styrene compound represented by chemical formula (V-1) to synthesize the thiophene compound of the present invention (see reaction schemes (E) and (F)).

Reaction Scheme (E)

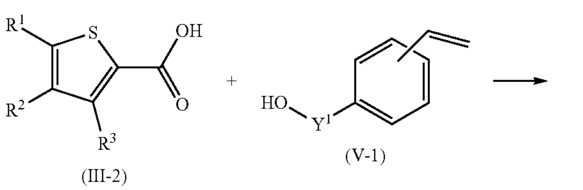

(III-2) (V-1) (I)

(wherein $R^1$, $R^2$, $R^3$, and $Y^1$ are as defined above.)

Reaction Scheme (F)

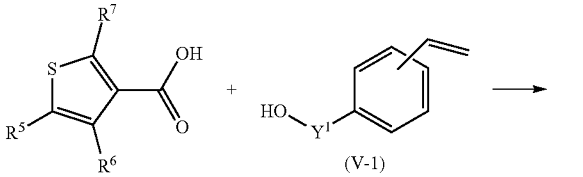

(IV-2) (V-1) (II)

(wherein $R^5$, $R^6$, $R^7$, and $Y^1$ are as defined above.)

In this reaction, the amount of the styrene compound represented by chemical formula (V-1) (the amount added) is preferably an appropriate proportion within the range of 0.8-fold to 2-fold mol relative to the amount of the thiophene compound represented by chemical formula (III-2) or chemical formula (IV-2) (the amount added).

In performing this reaction, a base (i) or a dehydration condensation agent (iv) may be used in order to facilitate the reaction. Additionally, a reaction solvent (v) may be used as necessary. The base (i) for use may be those listed as examples in Synthesis Method (1).

In this reaction, the amount of the base (i) (the amount added) is preferably an appropriate proportion within the range of 0.1-fold to 2-fold mol relative to the amount of the thiophene compound represented by chemical formula (III-2) or chemical formula (IV-2) (the amount added).

Examples of the dehydration condensation agent (iv) include phosphoric esters, such as diphenylphosphoryl azide, diethylphosphoryl cyanide, and diethyl cyanophosphate; carbodiimides, such as 1,3-dicyclohexyl carbodiimide, 1,3-diisopropyl carbodiimide, 1-ethyl-3-(3-dimethylaminopropyl) carbodiimide, and 1-ethyl-3-(3-dimethylaminopropyl) carbodiimide hydrochloride; and combinations of any of the carbodiimides listed above with an N-hydroxy compound, such as N-hydroxysuccinimide, 1-hydroxy benzotriazole, and N-hydroxy-5-norbornene-2,3-dicarboximide. These may be used singly, or in a combination of two or more.

The amount of the dehydration condensation agent (iv) (the amount added) is preferably an appropriate proportion within the range of 1-fold to 2-fold mol relative to the amount of the thiophene compound represented by chemical formula (III-2) or chemical formula (IV-2) (the amount added).

The reaction solvent (v) is not particularly limited as long as the reaction solvent (v) does not interfere with the reaction. Examples of the reaction solvent (v) include solvents such as benzene, toluene, xylene, dichloromethane, chloroform, carbon tetrachloride, dichloroethane, chlorobenzene, dichlorobenzene, ethyl formate, ethyl acetate, propyl acetate, butyl acetate, diethyl carbonate, diethyl ether, diisopropyl ether, tetrahydrofuran, dioxane, dimethoxyethane, diethylene glycol dimethyl ether, acetone, methyl ethyl ketone, methyl isobutyl ketone, isophorone, cyclohexanone, nitroethane, nitrobenzene, acetonitrile, isobutyronitrile, formamide, dimethylformamide, dimethylacetamide, hexamethylphosphorotriamide, dimethylsulfoxide, and sulfolane. These can be combined as necessary and used in an appropriate amount.

In this reaction, the reaction temperature is preferably set within the range of 0 to 80° C. The reaction time is set as appropriate according to the predetermined reaction temperature and is preferably set within the range of 1 to 72 hours.

After completion of the reaction, the thiophene compound of the present invention (desired product) can be taken out from the obtained reaction solution (reaction mixture) according to a means such as concentration of the reaction solution by distillation of the reaction solvent or solvent extraction.

Additionally, the thiophene compound of the present invention can be purified according to a means such as washing with water etc., activated carbon treatment, silica gel chromatography, or recrystallization as necessary.

Synthesis Method (4)

A thiophene compound represented by chemical formula (III-2) or chemical formula (IV-2) is reacted with a styrene compound represented by chemical formula (V-2) to synthesize the thiophene compound of the present invention (see reaction schemes (G) and (H)).

Reaction Scheme (G)

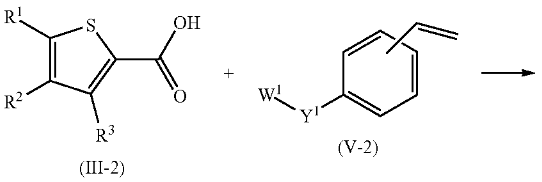

(III-2) (V-2)

-continued

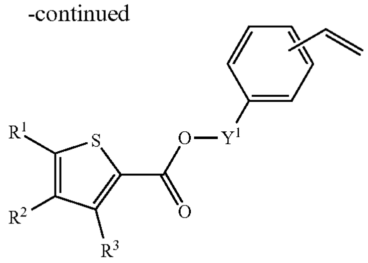

(I)

(wherein $R^1$, $R^2$, $R^3$, $Y^1$, and $W^1$ are as defined above.)

Reaction Scheme (H)

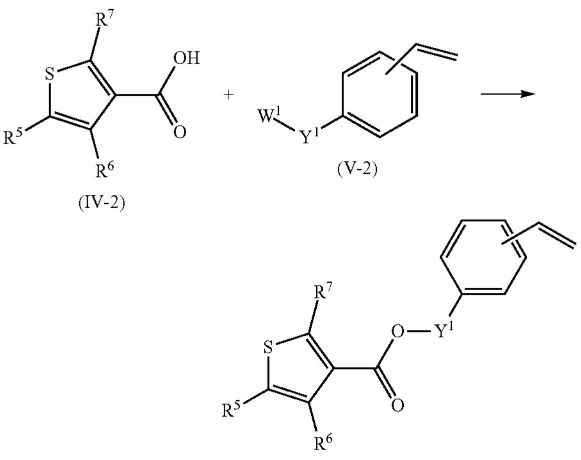

(IV-2) (V-2)

(II)

(wherein $R^5$, $R^6$, $R^7$, $Y^1$, and $W^1$ are as defined above.)

In this reaction, the amount of the styrene compound represented by chemical formula (V-2) (the amount added) is preferably an appropriate proportion within the range of 0.8-fold to 1.2-fold mol relative to the amount of the thiophene compound represented by chemical formula (III-2) or chemical formula (IV-2) (the amount added).

In performing this reaction, a base (i) may be used in order to facilitate the reaction. Additionally, a reaction solvent (ii) may be used as necessary. The base (i) and the reaction solvent (ii) for use may be those listed as examples in Synthesis Method (1).

A reaction accelerator (vi) may be used in combination with the base (i) in order to improve reactivity.

The amount of the base (i) (the amount added) is preferably an appropriate proportion within the range of 0.8-fold to 2-fold mol relative to the amount of the thiophene compound represented by chemical formula (III-2) or chemical formula (IV-2) (the amount added).

Examples of the reaction accelerator (vi) include alkali metal iodide salts, such as lithium iodide, sodium iodide, and potassium iodide; ammonium salt phase transfer catalysts, such as ethyl trimethyl ammonium bromide, ethyl trimethyl ammonium iodide, tetrabutyl ammonium bromide, tetrabutyl ammonium iodide, tetrahexyl ammonium bromide, and tetrahexyl ammonium iodide; phosphonium salt phase transfer catalysts, such as tetrabutyl phosphonium bromide and tetrabutyl phosphonium iodide; pyridine, and 4-dimethylamino pyridine. These may be used singly, or in a combination of two or more.

The amount of the reaction accelerator (vi) (the amount added) is preferably an appropriate proportion within the range of 0.01-fold to 5.0-fold mol, and more preferably 0.02-fold to 0.5-fold mol, relative to the amount of the styrene compound represented by chemical formula (V-2) (the amount added).

In this reaction, the reaction temperature is preferably set within the range of 0 to 100° C. The reaction time is set as appropriate according to the predetermined reaction temperature and is preferably set within the range of 1 to 48 hours.

After completion of the reaction, the thiophene compound of the present invention (desired product) can be taken out from the obtained reaction solution (reaction mixture) according to a means such as concentration of the reaction solution by distillation of the reaction solvent or solvent extraction.

Additionally, the thiophene compound of the present invention can be purified according to a means such as washing with water etc., activated carbon treatment, silica gel chromatography, or recrystallization as necessary.

The composition of the present invention contains the thiophene compound of the present invention as an essential component. The composition of the present invention may contain one or more types of the thiophene compound of the present invention.

The content of the thiophene compound of the present invention in the composition of the present invention is preferably 0.001 to 100 wt %.

Polymerizing the thiophene compound of the present invention provides a cured product. Allowing a curable compound different from the thiophene compound of the present invention (simply "curable compound" below) to be present together with the thiophene compound of the present invention during polymerization provides a cured product that is a copolymer of the thiophene compound of the present invention with the curable compound.

The curable compound encompasses both a polymerizable monomer and a polymerizable oligomer having the structure in which a polymerizable monomer is partially polymerized (semi-cured product).

Examples of polymerizable monomers include monofunctional (meth)acrylates, such as methyl (meth)acrylate, 2-hydroxyethyl (meth)acrylate, butyl (meth)acrylate, 4-hydroxybutyl (meth)acrylate, 2-ethylhexyl (meth)acrylate, ethylcarbitol (meth)acrylate, lauryl (meth)acrylate, phenoxyethyl (meth)acrylate, nonylphenoxy ethyl (meth)acrylate, 2-hydroxy-3-phenoxypropyl (meth)acrylate, dicyclopentenyl (meth)acrylate, isobornyl (meth)acrylate, N-n-butyl-O-(meth)acryloyloxyethyl carbamate, tetrahydrofurfuryl (meth)acrylate, acryloyl morpholine, trifluoroethyl (meth) acrylate, tribromobenzyl (meth)acrylate, perfluorooctylethyl (meth)acrylate, and isobornyl (meth)acrylate; silicon-containing (meth)acrylates, such as (meth)acryloxypropyl tris (methoxy)silane; alkylene glycol di(meth)acrylates, such as ethylene glycol di(meth)acrylate, propylene glycol di(meth) acrylate, neopentylglycol di(meth)acrylate, and 1,6-hexanediol di(meth)acrylate; polyalkyleneglycol di(meth)acrylates, such as triethylene glycol di(meth)acrylate, tripropylene glycol di(meth)acrylate, polyethylene glycol di(meth)acrylate, and polypropylene glycol di(meth)acrylate; polyfunctional (meth)acrylates, such as trimethylolpropane tri(meth) acrylate, dipentaerythritol pentaacrylate, pentaerythritol triacrylate, pentaerythritol tetraacrylate, ditrimethylol tetraacrylate, dipentaerythritol hexaacrylate, and polyisobornyl methacrylate; epoxy (meth)acrylates, such as ethylene glycol diglycidyl ether-epoxy (meth)acrylate, propylene glycol diglycidyl ether-epoxy di(meth)acrylate, phenol glycidyl ether-epoxy (meth)acrylate, resorcinol diglycidyl ether-epoxy (meth)acrylate, bisphenol A diglycidyl ether-epoxy di(meth)acrylate, and bis(4-hydroxyphenyl) sulfide diglycidyl ether-epoxy (meth)acrylate; epoxy (meth)acrylates that are reaction products of an epoxy compound with (meth)acrylic acid, such as phenol novolac epoxy resin-(meth)acrylate, cresol novolac epoxy resin-(meth)acrylate, bisphenol (e.g., bisphenol A and bisphenol F) epoxy resin-(meth)acrylate, biphenol (e.g., 3,3',5,5'-tetramethyl biphenol) epoxy resin-(meth)acrylate, and 1,3,5-tris(2,3-epoxypropyl) isocyanurate-(meth)acrylate; vinyl compounds, such as styrene, divinylbenzene, N-vinylpyrrolidone, and N-vinylcaprolactam; allyl group-containing compounds, such as ethylene glycol diallyl carbonate, trimellitic acid triallyl ester, and triallyl isocyanurate; urethane (meth)acrylates, polyurethane (meth)acrylates, thiourethane acrylates, polythiourethane acrylates, ester acrylates, polyester (meth)acrylates, polyether (meth)acrylates, sulfur-containing (meth) acrylates, and sulfur-containing polyfunctional (meth) acrylates.

The composition of the present invention contains the thiophene compound of the present invention as an essential component and may contain the curable compound described above as necessary. This curable compound for use may be a combination of the polymerizable monomer and polymerizable oligomer described above. The polymerizable monomer for use may be a combination of the polymerizable monomers described as examples above (which may be a combination of different types of polymerizable monomers), and the polymerizable oligomer for use may be a combination of different types of polymerizable oligomers.

In regards to the proportion of the content of the thiophene compound of the present invention and the content of the curable compound in the composition of the present invention, the content of the curable compound is preferably an appropriate proportion within the range of a 0-fold to 1000-fold amount (weight ratio), and more preferably an appropriate proportion within the range of a 0.01-fold to 100-fold amount (weight ratio) relative to the content of the thiophene compound of the present invention.

The method for curing (polymerizing) the composition of the present invention includes, for example, a radical polymerization method and an anion polymerization method.

The radical polymerization method includes a method of irradiation with active energy rays, such as light (LTV light, visible light), radioactive rays, electromagnetic waves, or electron beams, a method of heating, a method using a radical polymerization initiator, and a combination of these methods.

The radical polymerization initiator for use may be a photo-radical polymerization initiator or a thermal radical polymerization initiator, and may be added to the composition.

The photo-radical polymerization initiator for use can be any commonly used photo-radical polymerization initiator without any particular limitation. Examples include acetophenones, such as 2-hydroxy-2-methyl-1-phenylpropan-1-one, 1-hydroxycyclohexyl phenyl ketone, 2-(dimethylamino)-2-[(4-methylphenyl)methyl]-1-[4-(4-morpholinyl) phenyl]-1-butanone, and 2-methyl-1-[4-(methylthio) phenyl)]-2-morpholinopropan-1-one; benzoins, such as benzyl dimethyl ketal; benzophenones, such as benzophenone, 4-phenyl benzophenone, and hydroxy benzophenone; acyl phosphine oxides, such as 2,4,6-trimethylbenzoyl-diphenylphosphine oxide, bis(2,6-dimethoxybenzoyl)-2,4,4- trimethyl-pentylphosphine oxide, and bis(2,4,6-trimethylbenzoyl)-phenylphosphine oxide; thioxanthones, such as isopropylthioxanthone and 2,4-diethyl thioxanthone; and methylphenyl glyoxylate. These may be used in combination.

For the photo-radical polymerization initiator, known photopolymerization accelerators, such as benzoic acids (e.g., 4-dimethylaminobenzoic acid) or tertiary amines, may be used in combination, if necessary.

The content of the photo-radical polymerization initiator in the composition of the present invention is preferably a proportion of 0.001 to 20 wt %, and more preferably a proportion of 0.01 to 10 wt %.

The thermal radical polymerization initiator for use can be any commonly used thermal radical polymerization initiator without any particular limitation. Examples include diisopropyl peroxydicarbonate, benzoylperoxide, t-butyl peroxyisobutyrate, other peroxides, and azo compounds, such as azobisisobutyronitrile (AIBN). These may be used in combination.

The content of the thermal radical polymerization initiator in the composition of the present invention is preferably a proportion of 0.001 to 20 wt %, and more preferably a proportion of 0.01 to 10 wt %.

Optionally, in order to further increase the reaction rate, photo-radical polymerization (light curing) may be performed by using a photo-radical polymerization initiator before thermal radical polymerization (thermosetting) is performed by using the thermal radical polymerization initiator.

As long as the effects of the present invention are not impaired, the composition of the present invention may further contain the following: pigments (e.g., titanium white, cyanine blue, watching red, colcothar, carbon black, aniline black, manganese blue, iron black, ultramarine blue, Hansa red, chrome yellow, and chrome green); inorganic fillers (calcium carbonate, kaolin, clay, talc, mica, barium sulfate, lithopone, gypsum, zinc stearate, oxide, such as perlite, quartz, quartz glass, silica powder such as molten silica and spherical silica, spherical alumina, crushed alumina, magnesium oxide, beryllium oxide, titanium oxide, and zirconium oxide, nitrides, such as boron nitride, silicon nitride, and aluminum nitride, carbides, such as silicon carbide, hydroxides, such as aluminum hydroxide, and magnesium hydroxide, metals and alloys, such as copper, silver, iron, aluminum, nickel, and titanium, carbon materials, such as diamond and carbon); thermoplastic resin and thermosetting resin (homopolymers, such as high-density, medium-density, or low-density polyethylenes, polypropylene, polybutene, and polypentene, ethylene-propylene copolymers, polyamide resin, such as nylon-6 and nylon-6,6, vinyl chloride resin, nitrocellulose resin, vinylidene chloride resin, acrylic resin (including curable compounds, except for the polymerizable monomers described above), acrylamide resin, styrene resin, vinyl ester resin, polyester resin, phenolic resin (phenol compound), epoxy resin (epoxy compound), silicone resin, fluorine resin, elastomer resin, such as acrylic rubber and urethane rubber, and graft copolymers, such as methyl methacrylate-butadiene-styrene graft copolymers, and acrylonitrile-butadiene-styrene graft copolymers); reinforcing agents (e.g., glass fiber and carbon fiber); anti-drip agents (e.g., hydrogenated castor oil and particulate silicic anhydride); delusterants (e.g., fine powder silica and paraffin wax); grinding agents (e.g., zinc stearate); internal mold release agents (e.g., fatty acids, such as stearic acid, fatty acid metal salts, such as calcium stearate, fatty acid amides, such as stearic acid amide, fatty acid esters, polyolefin wax, and paraffin wax); diluents (e.g., organic solvents, such as n-butyl alcohol, methyl ethyl ketone (MEK), propylene glycol monomethyl ether acetate (PGMEA), and toluene, water, and combinations of an organic solvent with water); coupling agents (e.g., silane coupling agents, such as N-(2-aminoethyl)-3-aminopropyltrimethoxysilane and 3-glycidoxypropyltrimethoxysilane); chain transfer agents (e.g., thiol compounds, such as pentaerythritol tetrakis(3-mercaptopropionate)); and additives (modifiers), such as surfactants, leveling agents, antifoaming agents, fragrances, flame retardants, and dyes.

The thermoplastic resin and thermosetting resin encompass resins (compounds) with a cardo structure represented by chemical formula (VI) (a skeleton structure in which four aromatic rings are bound to a carbon atom).

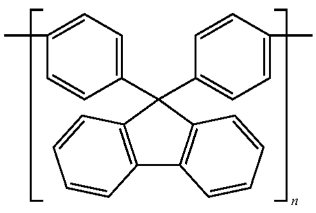

(VI)

(wherein n indicates the degree of polymerization.)

Examples of compounds with a cardo structure include monomers, such as 9,9-bis(4-glycidyloxyphenyl)fluorene, 9,9-bis(4-hydroxyphenyl)fluorene, 9,9-bis(4-hydroxy-3-methylphenyl)fluorene, 9,9-bis[4-(2-(meth)acryloyloxy-ethoxy)phenyl]fluorene, 9,9-bis[4-(3-(meth)acryloyloxy-2-hydroxypropoxy)phenyl]fluorene, 9,9-bis(cyanomethyl) fluorene, and 9,9-bis(3-aminopropyl)fluorene.

The method for preparing the composition of the present invention is not particularly limited. For example, the composition of the present invention can be prepared by mixing the thiophene compound of the present invention, a curable compound, a radical polymerization initiator, and additives, or by mixing a solution or dispersion of the thiophene compound of the present invention in a diluent (organic solvent), a curable compound, a radical polymerization initiator, and additives. Mixing means for use may be any known method.

Because the thiophene compound of the present invention is added, the composition of the present invention is prepared as a liquid (fluid) with a high degree of flowability and a low level of viscosity.

The kinematic viscosity (25° C.) of the composition can be adjusted to, for example, 20 to 300 mPa·s, or even 30 to 100 mPa-s. This can greatly improve the workability during the formation of a polymer from the composition.

Additionally, because the composition of the present invention contains a thiophene compound with a high refractive index, polymerizing the composition can provide a cured product with a high refractive index. Thus, the composition of the present invention is suitable as a material for use in the production of coating materials, ink, adhesives, tackifiers, gas barrier films, color filters, optical films, optical lenses, touch panels, and the like.

The coating materials are used in, for example, protection (hard coating) for touch panels, plastic containers, plastic sheets, plastic films, film liquid crystal devices, polarizers used in liquid crystal displays, optical components, or interior building materials (e.g., floor materials, wall materials, and artificial marble).

The ink is, for example, coloring ink, printing ink, TV ink, or inkjet ink. These inks are used in offset printing, flexographic printing, gravure printing, screen printing, inkjet printing, etc.

The adhesives are used in, for example, semiconductors, optics, optical components, optical waveguide coupling, optical waveguide peripheral component fixing, or CD/DVD bonding.

The tackifiers are used in, for example, adhesive (gluing) tapes, adhesive (gluing) sheets, or adhesive (gluing) labels.

The gas barrier films are used in, for example, electronic paper, flexible displays, organic EL devices, or organic solar cells.

The color filters are used in, for example, color liquid crystal displays (color filter on array (COA)), color image sensors, or organic EL displays.

The optical films are used in, for example, protective films for polarizers, films for liquid crystal displays, such as support films for prism sheets and light-guiding films, functional films, such as hard coating films, decorative films, and transparent conductive films, weather (light)-resistant films for solar cells, films for LED lighting or organic EL lighting, or transparent heat-resistant films for flexible electronics.

The optical lenses are used in, for example, lenses for microscopes, endoscopes, telescopes, cameras, or glasses, lenses for laser beam printers, lenses for sensors, prism lenses, or pickup lenses for optical discs.

The touch panels are used in, for example, personal computers, car navigation systems, cellular phones, electronic dictionaries, or office automation or factory automation equipment.

The composition of the present invention is also expected to have applications in raw materials or components, such as transparent materials, optical materials, dicing tapes, insulating materials (e.g., wire coating), solder resist ink, printed circuit boards, copper-clad laminates, copper foil with resin, prepregs, high-voltage insulating materials, interlayer insulating materials, passivation films for TFT, gate-insulating films for TFT, interlayer-insulating films for TET, transparent planarization films for TFT, packing for insulation, insulation coating materials, paint, UV powder paint, molding materials (e.g., sheets, films, and FRP), sealing materials, liquid crystal sealing materials, sealing materials for display devices, high-heat-resistant sealing materials, potting materials, sealant materials (semiconductor sealants, sealants for electrical materials, sealants for organic EL or LED devices, and sealants for various solar cells), resist materials (liquid resist materials, color resist materials, dry film resist materials, solder resist materials, and color filter resist materials), photo spacer materials for liquid crystal cells, optical molding, materials for solar cells, materials for fuel cells, display materials, recording materials, photosensitive drums for copiers, materials in the electrical or electronic field, such as solid electrolytes for batteries, materials for vibration isolators, waterproof materials, moisture-proof materials, heat-shrinkable rubber tubes, O-rings, gas separation membranes, concrete protection materials, linings, soil injection agents, cooling or heat storage materials, sealing materials for sterilization equipment, and oxygen-permeable membranes; and applications in additives (modifiers) for other (thermoplastic, thermosetting, or light-curing) resins or resin compositions.

EXAMPLES

The present invention is described in more detail below with reference to Examples and Comparative Example. However, the invention is not limited to these Examples.

The main starting materials used in the Examples and Comparative Example are as described below.

Main Starting Material

- Thiophene-2-carbonyl chloride (produced by Tokyo Chemical Industry Co., Ltd., see chemical formula (III-1-1))
- Thiophene-2-carboxylic acid (produced by Sigma-Aldrich, see the compound represented by chemical formula (III-2-1)) 4-Vinylbenzyl alcohol (synthesized according to the method described in WO2011/55792A, see the compound represented by chemical formula (V-1-1))
- A mixture of 4-chloromethylstyrene and 3-chloromethylstyrene (produced by AGC Seimi Chemical Co., Ltd., trade name: CMS-P, a mixture of a compound represented by chemical formula (V-2-1) and a compound represented by chemical formula (V-2-4)) Pyridine (produced by Fujifilm Wako Pure Chemical Corporation)
- Potassium carbonate (produced by Fujifilm Wako Pure Chemical Corporation)
- Dichloromethane (produced by Fujifilm Wako Pure Chemical Corporation)
- Dimethylformamide (produced by Fujifilm Wako Pure Chemical Corporation)
- (4-Vinylbenzyl)-2-naphthalene carboxylate (synthesized according to the method described in JPH01-118802A, see the compound represented by chemical formula (VII))

(VII)

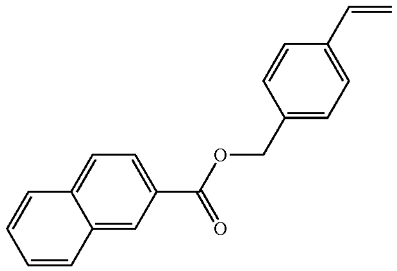

The methods for evaluation testing (measurement of refractive index and measurement of viscosity) used in the Examples and Comparative Example are as described below.

Measurement of Refractive Index

The compounds of the Examples and Comparative Example were individually dissolved in dimethylformamide (DMF) to give a concentration of 40 wt %, thereby preparing measurement samples (DMF solution).

The prepared DMF solutions and DMF alone were measured for refractive index (25° C.) in LED light (D-line wavelength) according to JIS K 0062 (Test Methods for Refractive Index of Chemical Products) with an Abbe refractometer (NAR-1T SOLID, produced by Atago Co., Ltd.).

From the obtained measurement values, the refractive index of the compounds of the Examples and Comparative Example was calculated according to the following formula.

Refractive index=(refractive index of DMF solution (compound concentration: 40 wt %)−refractive index of DMF alone)/0.4+refractive index of DMF alone Measurement of Viscosity The compounds were measured for kinematic viscosity at 25° C. with a viscometer (Rheosol-G5000, produced by UBM). Cases in which kinematic viscosity could not be measured (e.g., the compound being solid at 25° C.) were indicated as "N.D."

Example 1

Synthesis of (4-vinylbenzyl)-2-thiophenecarboxylate 11.27 g (84.0 mmol) of 4-vinylbenzyl alcohol and 100 mL of dichloromethane were added to a 300-mL three-neck flask. While the flask was cooled to 10° C., 7.04 g (89.0 mmol) of pyridine was added dropwise.

Subsequently, while the mixture was stirred at 10° C. or below, 11.73 g (80.0 mmol) of thiophene-2-carbonyl chloride was added dropwise, followed by stirring at room temperature for 12 hours.

Thereafter, the reaction solution was cooled with ice, and pyridine hydrochloride was filtered off, followed by concentration of the filtrate under reduced pressure. Subsequently, the concentrate was dissolved in 100 mL of toluene and washed with 50 mL of water. Thereafter, the organic layer was concentrated under reduced pressure.

The obtained concentrate was purified by silica gel column chromatography (toluene/hexane=1/2 (volume ratio)), thereby obtaining 14.50 g of a pale yellow liquid (yield: 74%).

The $^1$H-NMR spectral data of the obtained pale yellow liquid were as follows.

$^1$H-NMR ($CDCl_3$) δ: 7.83 (d, 1H), 7.55 (d, 1H), 7.41 (d, 4H), 7.09 (dd, 1H), 6.73 (dd, 1H), 5.76 (d, 1H), 5.33 (s, 2H), 5.26 (d, 1H).

The IR spectral data of the pale yellow liquid were as shown in the chart of FIG. 1.

From these spectral data, the obtained pale yellow liquid was identified as being the title thiophene compound represented by chemical formula (I-1).

Example 2

Synthesis of a mixture of (4-vinylbenzyl)-2-thiophenecarboxylate and (3-vinylbenzyl)-2-thiophenecarboxylate 14.10 g (110.0 nmol) of thiophene-2-carboxylic acid, 15.20 g (110.0 nmol) of potassium carbonate, and 100 mL of dimethylformamide were added to a 300-mL three-neck flask and heated to 50° C. While the mixture was stirred at 50° C., 15.26 g (100.00 mmol) of a mixture of 4-chloromethylstyrene and 3-chloromethylstyrene was added dropwise, followed by heating to 55° C. and stirring for 12 hours.

Thereafter, the reaction solution was cooled with ice, and the insoluble potassium chloride was filtered off. Subsequently, the filtrate was dissolved in 200 mL of toluene and washed with 100 mL of water. Thereafter, the organic layer was concentrated under reduced pressure, thereby obtaining 20.77 g of a pale yellow liquid (yield: 85%).

The $^1$H-NMR spectral data of the obtained pale yellow liquid were as follows.

$^1$H-NMR ($CDCl_3$) δ: 7.83 (d, 0.5H), 7.82 (d, 0.5H), 7.55 (d, 1H), 7.41 (m, 4H), 7.10 (dd, 0.5H), 7.09 (dd, 0.5H), 6.73 (dd, 0.5H), 6.71 (dd, 0.5H), 5.76 (d, 0.5H), 5.75 (d, 0.5H), 5.32 (s, 1H), 5.31 (s, 1H), 5.27 (d, 0.5H), 5.26 (d, 0.5H).

Figure 2:
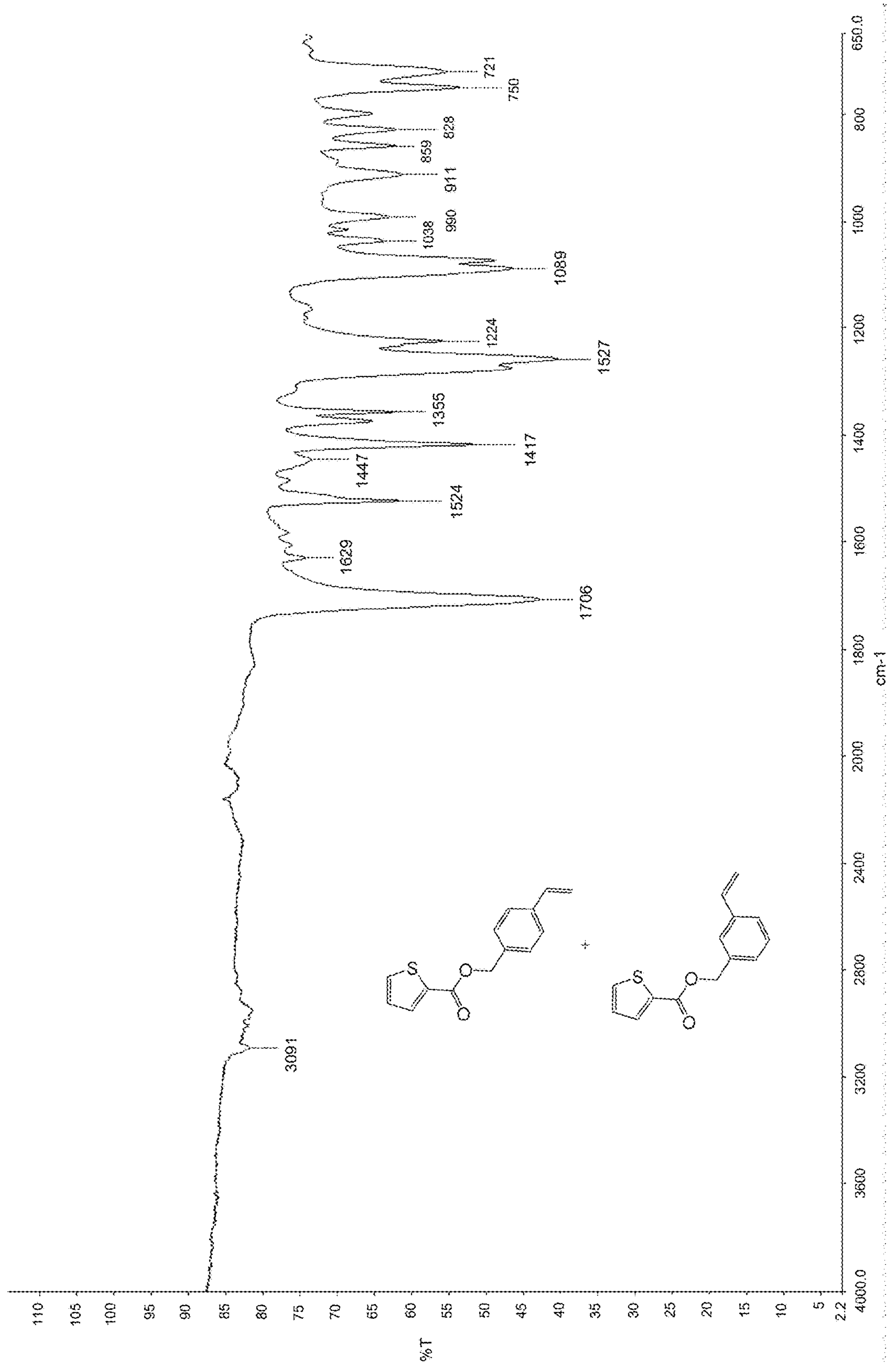
FIG. 2: An IR spectrum chart of the pale yellow liquid obtained in Example 2

The IR spectral data of the pale yellow liquid were as shown in the chart of FIG. 2.

From these spectral data, the obtained pale yellow liquid was identified as being a mixture of a thiophene compound represented by chemical formula (I-1) and a thiophene compound represented by chemical formula (I-2).

Example 3

The thiophene compound synthesized in Example 1 was subjected to an evaluation test (measurement of refractive index and measurement of viscosity). The obtained test results were as shown in Table 1.

Example 4

The thiophene compound synthesized in Example 2 was subjected to an evaluation test (measurement of refractive index and measurement of viscosity). The obtained test results were as shown in Table 1.

Comparative Example 1

A compound represented by chemical formula (VII) (pale orange solid) was subjected to an evaluation test (measurement of refractive index and measurement of viscosity). The obtained test results were as shown in Table 1. Because this compound was a solid at 25° C., the viscosity could not be measured and is thus indicated as "N.D."

TABLE 1

| | | Example 3 | Example 4 | Comparative Example 1 |
|---|---|---|---|---|
| Evaluation Test | Refractive Index (25° C.) | 1.64 | 1.64 | 1.62 |
| | Viscosity (25° C.) (mPa · s) | 14.0 | 10.4 | N.D. |

The results of Table 1 indicate that the thiophene compound of the present invention (the compounds of Examples 1 and 2) has a higher refractive index than conventional high-refractive materials (the compound represented by chemical formula (VII)).

Additionally, whereas the compound represented by chemical formula (VII) was a solid at 25° C., the thiophene compound of the present invention was found to be a liquid with a low level of viscosity.

INDUSTRIAL APPLICABILITY

The thiophene compound of the present invention has a low level of viscosity and can provide a cured product with a high level of refractive index.

Therefore, the composition of the present invention is suitable as a material for use in the production of coating materials, ink, adhesives, tackifiers, gas barrier films, color filters, optical films, optical lenses, touch panels, and the like.

The invention claimed is:

1. A thiophene compound represented by chemical formula (I) or chemical formula (II):

(I)

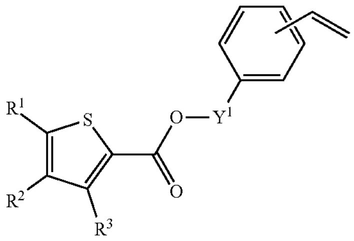

wherein $R^1$, $R^2$, and $R^3$ are identical or different and represent a hydrogen atom, —$OR^4$, —$SR^4$, —C(═O)—$R^4$, a phenyl group, a 2-thienyl group, or a 3-thienyl group, $R^2$ may be linked with $R^1$ or $R^3$ to form a ring containing a sulfur atom, together with two thiophene ring-forming carbon atoms to which $R^2$ and either $R^1$ or $R^3$ are bonded, $R^4$s are identical or different and represent a $C_{1-5}$ alkyl group, and $Y^1$ represents a single bond or a $C_{1-10}$ alkylene group; and (II)

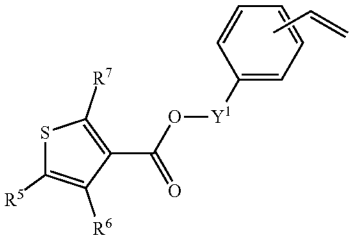

wherein $R^5$, $R^6$, and $R^7$ are identical or different and represent a hydrogen atom, —$OR^4$, —$SR^4$, —C(═O)—$R^4$, a phenyl group, a 2-thienyl group, or a 3-thienyl group, $R^5$ may be linked with $R^6$ to form a ring containing a sulfur atom, together with two thiophene ring-forming carbon atoms to which $R^5$ and $R^6$ are bonded, $R^4$s are identical or different and represent a $C_{1-5}$ alkyl group, and $Y^1$ represents a single bond or a $C_{1-10}$, alkylene group.

2. A method for synthesizing the thiophene compound of claim 1, the method comprising reacting a thiophene compound represented by chemical formula (III) or chemical formula (IV) with a styrene compound represented by chemical formula (V):

(III)

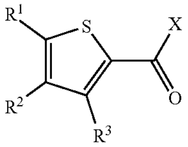

wherein $R^1$, $R^2$, and $R^3$ are as defined above, X represents a hydroxy group, a fluorine atom, a chlorine atom, a bromine atom, or an iodine atom;

(IV)

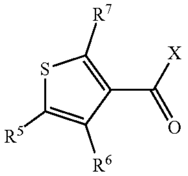

wherein $R^5$, $R^6$, and $R^7$ are as defined above, X represents a hydroxy group, a fluorine atom, a chlorine atom, a bromine atom, or an iodine atom; and (V)

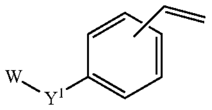

wherein $Y^1$ is as defined above, and W represents a hydroxy group, a fluorine atom, a chlorine atom, a bromine atom, or an iodine atom.

3. A composition comprising the thiophene compound of claim 1.

* * * * *